United States Patent [19]

Ichikawa et al.

[11] Patent Number: 5,606,079
[45] Date of Patent: Feb. 25, 1997

[54] PROCESS FOR THE SELECTIVE HYDROFORMYLATION OF TERMINAL OLEFIN GROUPS AND ITS USE IN THE PREPARATION OF 1,4-BUTANEDIAL MONOACETAL

[75] Inventors: Shuji Ichikawa; Akiko Fujita; Naoko Sumitani; Yuji Ohgomori, all of Ami-machi, Japan

[73] Assignee: Mitsubishi Chemical Corporation, Tokyo, Japan

[21] Appl. No.: 453,762

[22] Filed: May 30, 1995

[30] Foreign Application Priority Data

May 30, 1994 [JP] Japan .................................. 6-116690

[51] Int. Cl.$^6$ ................................ C07D 319/06
[52] U.S. Cl. ............................................ 549/375
[58] Field of Search ................................. 549/375

[56] References Cited

U.S. PATENT DOCUMENTS

| | | | |
|---|---|---|---|
| 3,929,915 | 12/1975 | Cumbo et al. | 260/630 E |
| 3,963,754 | 6/1976 | Cumbo et al. | 260/340.7 |
| 4,003,918 | 1/1977 | Hughes | 260/340.7 |
| 4,052,401 | 10/1977 | Hughes | 260/340.7 |

FOREIGN PATENT DOCUMENTS 6199730  7/1994  Japan .

OTHER PUBLICATIONS

Kollar, L. et al. *J. Organomet. Chem.* 441, 117–123 (1992).
Tosoh Corp. *Derwent* Abstract No. 94–269387, JP 06199730 (1994).

*Primary Examiner*—Mukund J. Shah
*Assistant Examiner*—King Lit Wong
*Attorney, Agent, or Firm*—Oblon, Spivak, McClelland, Maier & Neustadt, P.C.

[57] ABSTRACT

A process for producing 1,4-butanedial monoacetal by reacting acrolein acetal with a synthesis gas containing carbon monoxide and hydrogen, in the presence of a rhodium catalyst and an accelerator of formula (I)

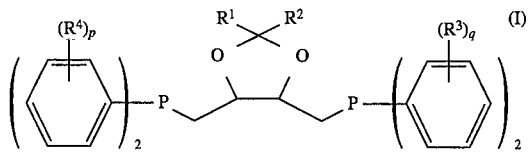

wherein $R^1$ and $R^2$ each, independently, denote a hydrogen atom, a $C_1$–$C_{20}$ alkyl group or a $C_6$–$C_{20}$ aryl group, or $R^1$ and $R^2$ together form a —$(CH_2)_n$— group, n is an integer of from 2 to 7, $R^3$ and $R^4$ each, independently, denote halogen or a trifluoromethyl group, and p and q are each, independently, an integer of from 0 to 3, which process can also be extended to the hydroformylation of other compounds which contain an olefin group in a terminal position.

24 Claims, No Drawings

PROCESS FOR THE SELECTIVE HYDROFORMYLATION OF TERMINAL OLEFIN GROUPS AND ITS USE IN THE PREPARATION OF 1,4-BUTANEDIAL MONOACETAL

BACKGROUND OF THE INVENTION

1. Field of the Invention

The present invention relates to an improved process for the selective hydroformylation of terminal carbons in a terminal olefin group and its use in preparing 1,4-butanedial monoacetal by the reaction of 2-propenal acetal (also known as acrolein acetal or 2-vinyl-5-methyl-1,3-dioxane) with synthesis gas using rhodium complex catalysts and specific organic phosphorus compounds.

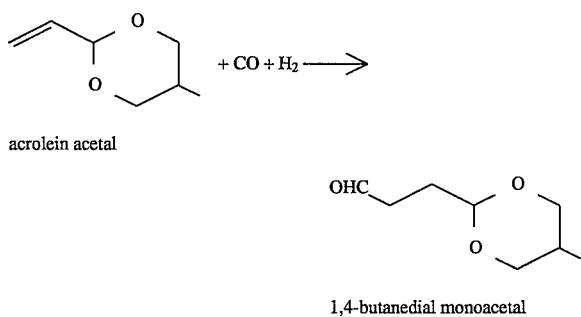

acrolein acetal 1,4-butanedial monoacetal

2. Discussion of the Background

Hydrolysis and hydrogenation of 1,4-butanedial monoacetal, as shown in U.S. Pat. No. 3,963,754, provides a mixture of 1,4-butanediol and 2-methyl-1,3-propanediol in high yield.

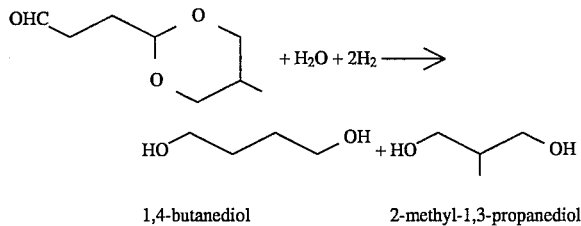

1,4-butanediol     2-methyl-1,3-propanediol 1,4-butanediol is a useful raw material for the production of various organic materials, such as tetrahydrofuran, polybutyleneterephthalate or polyurethanes.

Acrolein is known as a starting material for preparing 1,4-butanediol.

U.S. Pat. Nos. 3,929,915, 3,963,754 and JP-A-Sho 61-39613 report a three-step process for preparing 1,4-butanediol which comprises reaction of acrolein with 2-methyl-1,3-propanediol under conventional conditions to produce acrolein acetal (2-vinyl-5-methyl-1,3-dioxane) (Reaction 1), hydroformylation of the acrolein acetal under conventional conditions to produce the corresponding aldehydes (Reaction 2), and hydrolysis and hydrogenation of the aldehyde of 2-vinyl-5-methyl-1,3-dioxane under conventional conditions to obtain a mixture of 1,4-butanediol and 2-methyl-1,3-propanediol (Reaction 3).

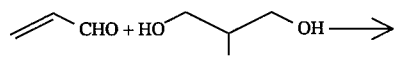 1)

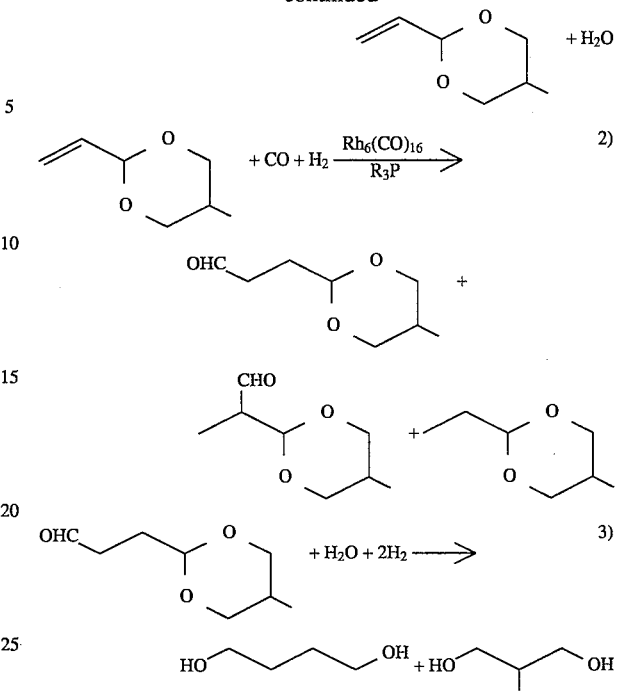

In Reaction 2 above, U.S. Pat. Nos. 3,929,915, 3,963,754, 4,052,401 and 4,003,918 describe that the hydroformylation reaction is carried out in the presence of a rhodium carbonyl complex catalyst $Rh_6(CO)_{16}$ with a phosphite ligand having a formula

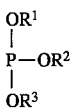

wherein $R^1$, $R^2$ and $R^3$ are the same or different and are $C_1$–$C_{12}$ alkyl groups or phenyl.

When acrolein acetal is hydroformylated, two isomers, 1,4-butanedial monoacetal and 2-methyl-1,3-propanedial monoacetal, are obtained as schematically shown above in Reaction 2. When 1,4-butanediol is produced through this reaction, the former is the desired compound. From this standpoint, it is important that the hydroformylation reaction is conducted to preferentially obtain the 1,4-butanedial monoacetal in a high yield.

U.S. Pat. No. 3,963,754 discloses that when using trimethyl phosphite as an accelerator of the reaction, a regioselectivity of 80% or more can be achieved with a molar ratio of starting acetal to rhodium catalyst of approximately 1,000. However, the phosphite compound is generally unstable under the hydroformylation reaction conditions (see U.S. Pat. No. 4,717,775). In fact, when trimethyl phosphite is used and a molar ratio of starting acetal to rhodium catalyst is set at approximately 10,000, not only is the prevalent selectivity notably decreased, but trimethyl phosphite is nearly non-detectable in the solution after reaction (see Comparative Example 2 below).

U.S. Pat. Nos. 4,003,918 and 4,052,401 describe that when the hydroformylation reaction is conducted in the presence of a catalyst which is a combination of a rhodium compound and triarylphosphine (wherein the aryl group is a phenyl group or an alkyl-substituted phenyl group) at a molar ratio of rhodium to acrolein acetal of from $1.25\times10^{-5}$ to $6.2\times10^{-2}$, preferably from $1.24\times10^{-4}$ to $1.24\times10^{-2}$, 3-formylpropanal acetal is obtained in a yield of approximately 85%. However, the yield thereof is not described in corresponding Examples. In fact, attempts to reproduce their results have shown that the regioselectivity corresponding to the yield described in these U.S. Patents is not reached at all (see Comparative Example 1 below).

SUMMARY OF THE INVENTION

Accordingly, one object of the present invention is to provide a process for the preparation of 1,4-butanedial monoacetal which provides high regioselectivity and product yield.

A further object of the present invention is to provide a process for the hydroformylation of terminal olefin groups with high regioselectivity and product yield.

These and other objects of the present invention has been satisfied by the discovery of a process for producing 1,4-butanedial monoacetal by the reaction of acrolein acetal with synthesis gas, wherein the hydroformylation reaction is carried out in the presence of a rhodium catalyst and an accelerator (an organic phosphorus compound) represented by formula (I)

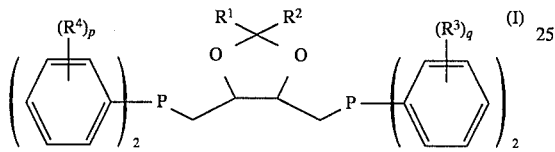

wherein $R^1$ and $R^2$ each denote a hydrogen atom, a $C_1$–$C_{20}$ alkyl group or a $C_6$–$C_{20}$ aryl group, or $R^1$ and $R^2$ together form a —$(CH_2)_n$— group, with n being an integer of from 2 to 7, $R^3$ and $R^4$ each denote halogen or a trifluoromethyl group, and p and q are each an integer of from 0 to 3.

DESCRIPTION OF THE PREFERRED EMBODIMENTS

The present invention relates to a process for the hydroformylation of the terminal carbon of a terminal olefin group with high regioselectivity and high yield. Preferably, the process is for the production of 1,4-butanedial monoacetal from acrolein acetal although it is also possible to use other terminal olefin group containing compounds as the starting material for use in hydroformylation to produce a corresponding hydroformylated product.

The preferred starting material which is used in a preferred embodiment of the present invention is acrolein acetal. The acetal group can be prepared under conventional conditions using a suitable alcohol. Suitable alcohols for use in the acetalization reaction include primary aliphatic alcohols such as methanol, ethanol, n-propanol and n-butanol; secondary aliphatic alcohols such as isopropanol, secondary butanol and isoamyl alcohol; alicyclic alcohols such as cyclopentanol and cyclohexanol; and diols such as ethylene glycol, 1,2-propylene glycol, 1,3-propanediol, 2-methyl-1, 3propanediol, 1,2-butanediol, 1,3-butanediol, 1,4-butanediol, 1,5-pentanediol and hexylene glycol. The acetal obtained from acrolein and the above-mentioned alcohols can be produced by known methods using an acid catalyst (such as described in Laid-Open Patent Application (Kokai) Nos. JP-A-Sho 51-59,614 and JP-A-Sho 51-125,005).

Rhodium Catalyst

The rhodium catalyst which is used in the process of the present invention is a carbonyl complex to which one or more molecules of carbon monoxide are bound as a ligand. Examples of the rhodium compound include hydridotetracarbonylrhodium, octacarbonyldirhodium, acetylacetonatodicarbonylrhodium, dodecacarbonyltetrarhodium and hexadecacarbonylhexarhodium. Also suitable are compounds which are converted to these carbonyl complexes under the hydroformylation reaction conditions of the present invention. Examples of such compounds include organic acid salts such as rhodium acetate, rhodium oxalate, rhodium formate and rhodium stearate, halides such as rhodium chloride, rhodium bromide and rhodium iodide, inorganic acid salts such as rhodium sulfate and rhodium nitrate, and metallic rhodium. The molar ratio of the catalyst to the starting olefin containing compounds such as acrolein acetal, is from 1 to $10^{-7}$, preferably from $10^{-1}$ to $10^{-6}$.

Organic Phosphorus Compound (Accelerator)

The organic phosphorus compound which is used in the process of the present invention has a structure represented by formula (I).

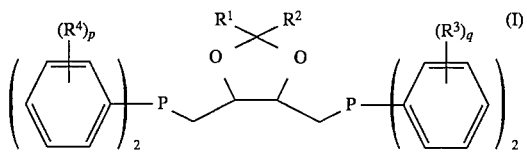

Preferred examples of the alkyl groups of $R^1$ and $R^2$ include methyl, ethyl, n-propyl, isopropyl, n-butyl, n-pentyl, n-hexyl, n-heptyl, n-octyl and n-dodecyl groups. Preferred examples of the aryl group include phenyl, tolyl, xylyl, mesityl and naphthyl groups. Preferred examples of the —$(CH_2)_n$— group formed by $R^1$ and $R^2$ in combination include cyclopropylidene, cyclobutylidene, cyclopentylidene, cyclohexylidene and cycloheptylidene.

Specific examples of the halogens of $R^3$ and $R^4$ include a fluoro group, a chloro group and a bromo group.

Preferred examples of the organic phosphorus compound represented by formula (I) include 2,3-o-isopropylidene-2,3-dihydroxy-1,4-bis(diphenylphosphino)butane, 2,3-o-cyclohexylidene-2,3-dihydroxy-1,4-bis(diphenylphosphino) butane and 2,3-o-benzylidene-2,3-dihydroxy-1,4-bis (diphenylphosphino)butane.

The organic phosphorus compound can be easily synthesized from a tartaric acid ester and a carbonyl compound via ketalization, reductive hydrogenation and toluenesulfonylation using conventional methods such as described by H. B. Kagan and T-P. Dang, in "Journal of the American Chemical Society," 94, 6429 (1972)].

The optimum amount of the organic phosphorus compound used varies depending on the concentration of the catalyst or the reaction conditions. The molar ratio of the organic phosphorus compound to the rhodium catalyst is preferably from 0.1 to 10,000, more preferably from 0.5 to 1,000.

Solvent

The present reaction is preferably performed in the absence of a solvent. But if required, a solvent that does not react with the starting olefin containing compound, such as the above-noted acrolein acetal, can be used. Examples of the solvent include saturated hydrocarbons such as hexane, aromatic hydrocarbons such as benzene and toluene; mono alcohols such as methanol, ethanol, propanol and butanol; diols such as ethylene glycol, propylene glycol, butanediol and hexylene glycol; ethers such as diethyl ether, tetrahydrofuran and dioxane; esters such as methyl acetate, ethyl acetate, butyrolactone and tricaprylin; amides such as dimethylformamide, dimethylacetamide and methylpyrrolidinone; and ureas such as dimethylimidazolidinone and tetramethylurea.

Hydroformylation Reaction Conditions

In a preferred embodiment, the hydroformylation reaction of 2-propenal acetal and a mixed gas of carbon monoxide and hydrogen is carried out in the presence of the rhodium catalyst and the accelerator represented by formula (I). The carbon monoxide/hydrogen molar ratio is from 0.1 to 10, preferably from 0.5 to 8. The reaction proceeds well at a partial pressure of the mixed gas of 1 atm or less. However, in order to obtain a higher reaction rate, the reaction is preferably conducted at a higher pressure. On the other hand, for ensuring a satisfactory regioselectivity for the terminal position of the olefin group, it is desirable to use a pressure which is not too high. Accordingly, the partial pressure of the mixed gas which is used in the reaction is preferably from 0.1 to 150 bar, more preferably from 0.5 to 50 bar. The mixed gas does not necessarily have to be of high-purity with respect to the carbon monoxide and hydrogen, and it may contain an optional amount of an inert gas that does not hinder the desired reaction. Suitable examples of the inert gas include nitrogen, carbon dioxide and argon.

The reaction will proceed even at room temperature. However, in order to obtain a higher reaction rate, the reaction is usually conducted while heating. The reaction temperature is preferably from 10° to 200° C., more preferably from 20° to 150° C. Since the reaction time varies depending on the reaction conditions, completion of the reaction is normally determined at the time at which absorption of the gas is no longer observed. The reaction time is generally from 0.1 to 50 hours, preferably from 0.2 to 30 hours.

Reaction Product

In the preferred embodiment of reaction of acrolein acetal, the compounds which are observed as reaction products are: (1) 1,4-butandial monoacetal, (2) 2-methyl -1,3-propanedial monoacetal, and (3) 2-propanal acetal. Other than these three compounds, trace amounts of high-boiling compounds can also be formed. These reaction products can be separated from the catalyst by conventional methods such as distillation, extraction or adsorption.

In the preferred embodiment of the present invention, the terminal carbon of the olefin in 2-propenal acetal can be hydroformylated with a higher selectivity using a smaller amount of a catalyst than in conventional methods, and 1,4-butanedial monoacetal can be advantageously produced with industrially significant improvements in selectivity and yield. The 1,4-butanedial monoacetal produced can then be converted to a profitable chemical product such as 1,4-butanediol, tetrahydrofuran, or butyrolactone, which are useful as starting materials in the production of various polymers, such as polyesters, via hydrolysis and reduction.

Having generally described this invention, a further understanding can be obtained by reference to certain specific examples which are provided herein for purposes of illustration only and are not intended to be limiting unless otherwise specified.

Examples

In the following Examples and Comparative Examples, conversion, selectivity and linearity are defined as follows.

$$\text{Conversion} = 100 \times \frac{\text{Amount of starting material reacted (mols)}}{\text{Amount of starting material charged (mols)}}$$

$$\text{Selectivity} = 100 \times \frac{\text{Amount of hydroxyformylated product (mols)}}{\text{Amount of starting material reacted (mols)}}$$

$$\text{Linearity} = 100 \times \frac{\text{Amount of 1,4-butanedial monoacetal formed (mols)}}{\text{Amount of hydroformylated product (mols)}}$$

Example 1

A 30-ml stainless steel autoclave was charged with 4,245 g (33.12 mmols) of acrolein acetal, 0.5 mg (0.0020 mmol) of acetylacetonatodicarbonylrhodium and 1.6 mg (0.0032 mmol) of 2,3-o-isopropylidene-2,3-dihydroxy-1,4-bis-(diphenylphosphino)butane, and sealed. The gaseous phase within the system was replaced with a mixed gas of carbon monoxide and hydrogen (at a molar ratio of 1:1). The mixed gas was added up to a pressure of 10 bar. While stirring, the reaction was conducted at 100° C. for 2 hours. During this time, the gas being absorbed was supplemented from outside, in order to maintain the pressure of the reaction at 10 bar.

The reactor was cooled to room temperature and opened to obtain a homogenous solution. Quantitative analysis of the product by gas chromatography showed 0.01 mmol of unreacted acrolein acetal, 25.95 mmols of 2-(2-formylethyl)-5-methyl-1,3-dioxane, 6.92 mmols of 2-(1-formylethyl)-5-methyl-1,3-dioxane and 0.23 mmol of 2-ethyl-5-methyl-1,3-dioxane. The conversion was approximately 100%, the selectivity was 99.3% and the linearity was 79.0%.

Examples 2 to 13 and Comparative Example 1

The hydroformylation reaction was conducted in the same manner as in Example 1 except that the amounts of acrolein acetal and acetylacetonatodicarbonylrhodium and the kind and amount of the phosphine compound used as a cocatalyst were changed as shown in Table 1 and the reaction conditions shown in Table 2 were used. The results are shown in Table 2 along with the results in Example 1.

TABLE 1

| | Amount of acrolein acetal* [g(mols)] | Amount of acetylacetonato dicarbonylrhodium [mg(mmol)] | Phosphine Compound (amount: mmol) | | Phosphine (mol) Rhodium (g-atom) | Starting material (mol) Rhodium (g-atom) |
|---|---|---|---|---|---|---|
| Example 1 | 4.245 (33.12) | 0.50 (0.0020) | 2,3-o-isopropylidene-2,3-dihydroxy-1,4-bis(diphenylphosphino)butane | (0.0032) | 1.6 | 16,658 |
| Example 2 | 4.714 (36.78) | 0.46 (0.0018) | 2,3-o-cyclohexylidene-2,3-dihydroxy- | (0.0037) | 2.0 | 20,193 |

TABLE 1-continued

| | Amount of acrolein acetal* [g(mols)] | Amount of acetylacetonato dicarbonylrhodium [mg(mmol)] | Phosphine Compound (amount: mmol) | | Phosphine (mol) Rhodium (g-atom) | Starting material (mol) Rhodium (g-atom) |
|---|---|---|---|---|---|---|
| Example 3 | 4.262 (33.25) | 0.44 (0.0017) | 2,3-o-benzylidene-2,3-dihydroxy-1,4-bis(diphenylphosphino)butane | (0.0032) | 1.9 | 19,681 |
| Example 4 | 4.193 (32.71) | 0.44 (0.0017) | 2,3-o-benzylidene-2,3-dihydroxy-1,4-bis(diphenylphosphino)butane | (0.0084) | 5.0 | 19,585 |
| Example 5 | 4.316 (33.67) | 0.077 (0.0003) | 2,3-o-isopropylidene-2,3-dihydroxy-1,4-bis(diphenylphosphino)butane | (0.0033) | 10.0 | 101,145 |
| Example 6 | 4.259 (33.22) | 0.077 (0.0003) | 2,3-o-isopropylidene-2,3-dihydroxy-1,4-bis(diphenylphosphino)butane | (0.0018) | 5.1 | 101,612 |
| Example 7 | 4.420 (34.84) | 0.077 (0.0003) | 2,3-o-isopropylidene-2,3-dihydroxy-1,4-bis(diphenylphosphino)butane | (0.0018) | 5.1 | 99,894 |
| Example 8 | 4.282 (33.41) | 0.077 (0.0003) | 2,3-o-isopropylidene-2,3-dihydroxy-1,4-bis(diphenylphosphino)butane | (0.0032) | 9.6 | 100,353 |
| Example 9 | 4.296 (33.51) | 0.077 (0.0003) | 2,3-o-isopropylidene-2,3-dihydroxy-1,4-bis(diphenylphosphino)butane | (0.0032) | 9.6 | 100,648 |
| Example 10 | 4.329 (33.77) | 0.077 (0.0003) | 2,3-o-isopropylidene-2,3-dihydroxy-1,4-bis(diphenylphosphino)butane | (0.0016) | 4.8 | 100,268 |
| Example 11 | 4.726 (36.87) | 0.103 (0.0004) | 2,3-o-cyclohexylidene-2,3-dihydroxy-1,4-bis(diphenylphosphino)butane | (0.0037) | 10.1 | 100,665 |
| Example 12 | 4.939 (38.53) | 0.103 (0.0004) | 2,3-o-cyclohexylidene-2,3-dihydroxy-1,4-bis(diphenylphosphino)butane | (0.0067) | 17.5 | 101,073 |
| Example 13 | 4.560 (35.57) | 0.077 (0.0003) | 2,3-o-cyclohexylidene-2,3-dihydroxy-1,4-bis(diphenylphosphino)butane | (0.0033) | 9.8 | 104,627 |
| Comp. Ex. 1 | 3.326 (25.94) | 0.30 (0.0013) | triphenylphosphine | (0.25) | 195.6 | 20,285 |
| Comp. Ex. 2** | 4.489 (35.02) | 0.88 (0.0035) | trimethylphosphite | (0.18) | 51.5 | 10,040 |

*2-vinyl-5-methyl-1,3-dioxane.
**2-vinyl-4-methyl-1,3-dioxane.

TABLE 2

| | Reaction temperature [°C.] | Reaction time [hrs] | Pressure of CO/H$_2$ [bar]*** | Conversion (%) | Selectivity (%) | Linearity (%) |
|---|---|---|---|---|---|---|
| Example 1 | 100 | 2.0 | 10.0 | 100 | 99.3 | 79.0 |
| Example 2 | 100 | 1.5 | 10.0 | 99.4 | 99.3 | 79.3 |
| Example 3 | 100 | 2.0 | 4.0 | 100 | 98.5 | 84.2 |
| Example 4 | 100 | 2.0 | 4.0 | 100 | 98.7 | 81.0 |
| Example 5 | 110 | 3.0 | 10.0 | 97.3 | 99.7 | 77.3 |
| Example 6 | 110 | 2.5 | 4.0 | 98.8 | 98.6 | 79.7 |
| Example 7 | 100 | 6.0 | 4.0 | 99.7 | 98.3 | 78.7 |
| Example 8 | 100 | 6.0 | 2.0 | 99.6 | 98.8 | 81.7 |
| Example 9 | 110 | 4.0 | 2.0 | 100 | 96.4 | 82.4 |
| Example 10 | 110 | 4.0 | 2.0 | 96.9 | 97.0 | 83.8 |
| Example 11 | 110 | 4.0 | 2.0 | 99.0 | 97.4 | 85.3 |
| Example 12 | 110 | 4.0 | 2.0 | 99.9 | 97.8 | 83.0 |
| Example 13 | 110 | 4.5 | 1.0 | 99.8 | 95.2 | 86.4 |
| Comp. Ex. 1 | 100 | 2.0 | 10.0 | 73.7 | 94.4 | 58.8 |
| Comp. Ex. 2 | 100 | 3.0 | 10.0 | 77.8 | 95.4 | 77.8 |

***Pressure of a CO/H$_2$ mixed gas (at a molar ratio of 1:1)

Comparative Example 2

A 30-ml stainless steel autoclave was charged with 4.489 g (35.02 mmols) of 2-vinyl-4-methyl-1,3-dioxane, 0.88 mg (0.0035 mmol) of acetylacetonatodicarbonylrhodium and 22.3 mg (0.1797 mmol) of trimethyl phosphite, and sealed. The gaseous phase within the system was replaced with a mixed gas of carbon monoxide and hydrogen (at a molar ratio of 1:1), and the mixed gas was added to provide a pressure of 10 bar. While stirring, the reaction was conducted at 100° C. for 3 hours. During this time, the gas being absorbed was supplemented from outside, in order to maintain the reactor at a pressure of 10 bar. The reactor was cooled to room temperature and opened to obtain a homogenous solution. Quantitative analysis of the product by gas chromatography showed 7.76 mmols of unreacted 2-vinyl-4-methyl-1,3-dioxane, 19.95 mmols of 2-(2-formylethyl)-4-methyl-1,3-dioxane, 6.04 mmols of 2-(1-formylethyl)-4-methyl-1,3-dioxane and 0.51 mmol of 2-ethyl-4-methyl-1,3-dioxane. The conversion was approximately 77.8% the selectivity was 95.4%, and the linearity was 77.8%.

Obviously, additional modifications and variations of the present invention are possible in light of the above teachings. It is therefore to be understood that within the scope of the appended claims, the invention may be practiced otherwise than as specifically described herein.

What is claimed and desired to be secured by Letters Patent of the United States is:

1. A process for producing 1,4-butanedial monoacetal comprising reacting acrolein acetal with synthesis gas containing carbon monoxide and hydrogen in the presence of a rhodium catalyst and an accelerator represented by formula (I)

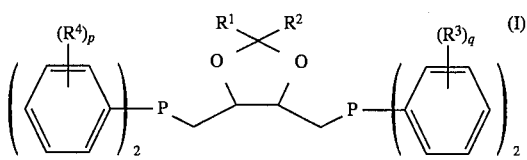

wherein $R^1$ and $R^2$ each, independently, denote a hydrogen atom, a $C_1$–$C_{20}$ alkyl group or a $C_6$–$C_{20}$ aryl group, or $R^1$ and $R^2$ together form a —$(CH_2)_n$— group, n is an integer of from 2 to 7, $R^3$ and $R^4$ each, independently, denote halogen or a trifluoromethyl group, and p and q are each, independently, an integer of from 0 to 3.

2. The process of claim 1, wherein the accelerator represented by formula (I) is a compound selected from the group consisting of 2,3-o-isopropylidene-2,3-dihydroxy-1,4-bis(diphenylphosphino) butane, 2,3-o-cyclohexylidene-2,3-dihydroxy-1,4-bis(diphenylphosphino)butane, and 2,3-o-benzylidene-2,3-dihydroxy-1,4-bis(diphenylphosphino)butane.

3. The process of claim 1, wherein the rhodium catalyst is a compound selected from the group consisting of acetylacetonatodicarbonylrhodium, hydridotetracarbonylrhodium, octacarbonylrhodium, dodecacarbonylrhodium, and hexadecacarbonylhexarhodium.

4. The process of claim 1, wherein the rhodium catalyst is present in an amount sufficient to provide a molar ratio of rhodium catalyst to acrolein acetal of from 1 to $10^{-7}$.

5. The process of claim 4, wherein the molar ratio of rhodium catalyst to acrolein acetal is from $10^{-1}$ to $10^{-6}$.

6. The process of claim 1, wherein the accelerator is present in an amount sufficient to provide a molar ratio of accelerator to rhodium catalyst of from 0.1 to 10,000.

7. The process of claim 6, wherein the molar ratio of accelerator to rhodium catalyst is from 0.5 to 1000.

8. The process of claim 1, wherein the reaction is carried out in the presence of a solvent selected from the group consisting of saturated hydrocarbons, aromatic hydrocarbons, monoalcohols, diols, ethers, esters, amides and ureas.

9. The process of claim 1, wherein the reaction is carried out in the absence of a solvent.

10. The process of claim 1, wherein the synthesis gas contains a molar ratio of carbon monoxide/hydrogen of from 0.1 to 10.

11. The process of claim 10, wherein the carbon monoxide/hydrogen ratio is from 0.5 to 8.

12. The process of claim 1, wherein the reaction is carried out at a partial pressure of synthesis gas of 0.1 atm to 150 bar.

13. The process of claim 12, wherein the partial pressure of synthesis gas is from 0.5 to 50 bar.

14. The process of claim 3, wherein the accelerator represented by formula (I) is a compound selected from the group consisting of 2,3-o-isopropylidene-2,3-dihydroxy-1,4-bis(diphenylphosphino) butane, 2,3-o-cyclohexylidene-2,3-dihydroxy-1,4-bis(diphenylphosphino)butane, and 2,3-o-benzylidene-2,3-dihydroxy-1,4-bis(diphenylphosphino) butane.

15. The process of claim 3, wherein the rhodium catalyst is present is present in an amount sufficient to provide a molar ratio of rhodium catalyst to acrolein acetal of from 1 to $10^{-7}$.

16. The process of claim 15, wherein the molar ratio of rhodium catalyst to acrolein acetal is from $10^{-1}$ to $10^{-6}$.

17. The process of claim 3, wherein the accelerator is present in an amount sufficient to provide a molar ratio of accelerator to rhodium catalyst of from 0.1 to 10,000.

18. The process of claim 17, wherein the molar ratio of accelerator to rhodium catalyst is from 0.5 to 1000.

19. The process of claim 3, wherein the reaction is carried out in the presence of a solvent selected from the group consisting of saturated hydrocarbons, aromatic hydrocarbons, monoalcohols, diols, ethers, esters, amides and ureas.

20. The process of claim 3, wherein the reaction is carried out in the absence of a solvent.

21. The process of claim 3, wherein the synthesis gas contains a molar ratio of carbon monoxide/hydrogen of from 0.1 to 10.

22. The process of claim 21, wherein the carbon monoxide/hydrogen ratio is from 0.5 to 8.

23. The process of claim 3, wherein the reaction is carried out at a partial pressure of synthesis gas of 0.1 atm to 150 bar.

24. The process of claim 23, wherein the partial pressure of synthesis gas is from 0.5 to 50 bar.

* * * * *